US00PP12168P2

(12) United States Plant Patent
Molyneux

(10) Patent No.: US PP12,168 P2
(45) Date of Patent: Oct. 30, 2001

(54) LEPTOSPERMUM PLANT NAMED 'BY11'

(76) Inventor: William Mitchell Molyneux, P.O. Box 365, Yarra Glenn, Victoria 3775 (AU)

( * ) Notice: Subject to any disclaimer, the term of this patent is extended or adjusted under 35 U.S.C. 154(b) by 0 days.

(21) Appl. No.: 09/484,287

(22) Filed: Jan. 18, 2000

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Leptospermum plant named 'BY11' characterized by its compact and mostly upright plant habit with terminals occasionally weeping; closely-spaced small leaves, densely foliated; numerous light pink flowers; and relatively high concentrations of citronellal and/or its analogs, pulegol and isopulegol.

1 Drawing Sheet

BACKGROUND OF THE INVENTION

The present Invention relates to a new and distinct cultivar of Leptospermum plant, botanically known as *Leptospermum liversidgei*, and hereinafter referred to by the cultivar name 'BY11'.

The new Leptospermum is a product of a planned and controlled breeding program conducted by the Inventor in Montrose, Victoria, Australia. The objective of the breeding program is to create new Leptospermums with and compact and upright plant habit and containing high concentrations of citronellal and/or the citronellal analogs, pulegol and isopulegol. These essential oils have effective Mosquito-repellant properties.

The new cultivar originated from a self-pollination by the Inventor of the Inventor's proprietary selection of *Leptospermum liversidgei* identified as 'BY18'. The cultivar 'BY11' was discovered and selected by the Inventor as a plant within the progeny of the stated self-pollination in a controlled environment in Montrose, Victoria, Australia.

Asexual reproduction of the new cultivar by vegetative cuttings taken at Montrose, Victoria, Australia, has shown that the unique features of this new Leptospermum are stable and reproduced true to type in successive generations.

SUMMARY OF THE INVENTION

Plants of the cultivar 'BY11' have not been observed under all possible environmental conditions. The phenotype may vary somewhat with variations in environment such as temperature, light intensity, daylength, and fertilizer rate without, however, any variance in genotype.

The following traits have been repeatedly observed and are determined to be the unique characteristics of 'BY11'. These characteristics in combination distinguish 'BY11' as a new and distinct cultivar:

1. Compact and mostly upright plant habit; terminals occasionally weeping.

2. Closely-spaced small leaves; densely foliated.

3. Numerous light pink flowers.

4. Relatively high concentrations of citronellal and/or its analogs, pulegol and isopulegol.

In side-by-side comparisons conducted by the Inventor in Montrose, Victoria, Australia, the following differences between the new Leptospermum and the parent selection, 'BY18', have been observed:

1. Plants of the new Leptospermum are compact and are mostly upright whereas plants of the selection 'BY18' have an open, outwardly spreading and weeping plant habit.

2. Plants of the new Leptospermum are more densely-foliated than plants of the selection 'BY18'.

3. New vegetative growth of plants of the new Leptospermum is green whereas new vegetative growth of the selection 'BY11' is reddish.

4. Plants of the new Leptospermum and plants of the selection 'BY18' differ in flower color.

5. Plants of the new Leptospermum have a higher concentration of citronellal, pulegol and/or isopulegol than plants of the selection 'BY18'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Leptospermum.

The photograph at the top of the sheet comprises a side perspective view of typical plants of the 'BY11', left, and the parent selection, 'BY18', right.

The photograph at the bottom of the sheet comprises a close-up view of typical flowering stems of 'BY11'.

DETAILED BOTANICAL DESCRIPTION

The following observations, measurements and values describe three-year old plants of the new cultivar that were propagated in a double polyethylene-covered greenhouse and grown in 20-cm containers under outdoor conditions with day temperatures ranging from 8 to 44° C. and night temperatures ranging from 0 to 18° C. Color references are made to The Royal Horticultural Society Colour Chart except where general terms of ordinary dictionary significance are used.

Botanical classification: *Leptospermum liversidgei* cultivar 'BY11'.

Parentage: Self-pollination of the Inventor's proprietary selection of *Leptospermum liversidgei* identified as 'BY18', not patented.

Propagation:

*Type cutting.*—Vegetative cuttings.

*Time to initiate roots.*—Summer: About 30 days at temperatures of 35° C. Winter: About 40 days at temperatures of 18° C.

*Time to produce a rooted liner.*—Summer: About 45 days at temperatures of 35° C. Winter: About 55 days at temperatures of 18° C.

*Root description.*—Fibrous, freely branching.

Plant description:

*Form.*—Compact and mostly upright plant habit; terminals occasionally weeping.

*Plant height* (*from soil level to top of plant plane*).—About 1.2 meters.

*Area of spread.*—About 80 cm.

*Vigor.*—Moderate.

*Branching habit.*—Freely branching; pinching enhances branching.

*Lateral branch description.*—Length: About 50 cm. Texture: Smooth, glabrous. Color: Gray.

*Foliage description.*—Leaves simple, alternate, generally symmetrical, durable and long persisting. Quantity: About 80 per 10 cm of stem. Length: About 3 to 8 cm. Width: About 1.5 to 3.5 cm. Shape: Lanceolate. Apex: Softly mucronate to obtuse. Base: Tapering to short petiole, nearly sessile. Margin: Entire. Texture: Smooth, glabrous; flexible; prominent midvein. Fragrance: Citrus-like. Color: Young foliage, upper and lower surfaces: 144C. Mature foliage, upper and lower surfaces: 147B. Petiole: Length: Minute to 0.75 mm. Diameter: About 0.3 mm. Color: Green.

Flower description:

*Flower type and habit.*—Light pink single purple flowers; axillary; flowers face outward. Flowers persistent. Flowering continuous. Flowers nearly sessile or with very short peduncles.

*Natural flowering season.*—Flowering occurs during the late spring and summer.

*Quantity.*—Very freely flowering, about four open flowers per 12 cm of stem.

*Fragrance.*—Slight; typical of species.

*Flower longevity on the plant.*—About two to three weeks.

*Flower longevity as a cut flower.*—About one week.

*Flower size.*—Diameter: About 1.3 to 1.8 cm. Height (depth): About 3 to 5 mm.

*Flower buds.*—Length: About 4 to 6 mm. Diameter: About 3 to 4 mm. Shape: Roughly spherical, dome-like. Color: 50C.

*Petals.*—Arrangement: Five-parted. Length: About 5 to 7 mm. Width: About 4 to 5 mm. Shape: Broadly rhomboidal, tapering narrowly at base. Apex: Rounded or blunt. Margin: Slightly fringed and occasionally wavy. Texture: Smooth, soft; glabrous. Color: Upper and lower surfaces, when opening: 56B to 56C to 56D. Upper and lower surfaces, opened flower: 56D.

*Sepals/calyx.*—Calyx length: About 3 to 5 mm. Calyx width: About 3 to 4 mm. Sepal length: About 1.5 mm. Sepal width: About 1.5 to 1.7 mm. Sepal quantity: Five. Sepal shape: Triangular. Sepal apex: Pointed. Sepal margin: Fringed. Sepal texture: Smooth; thick. Sepal color: Upper surface: 149B; margin, 56B. Lower surface: 50C.

*Peduncle.*—Angle: About 35° to stem. Length: Minute to about 0.5 mm. Color: Green.

*Reproductive organs.*—Stamens: Stamen number: About 15 to 20. Anther length: About 0.3 mm. Anther color: Yellow. Pollen color: Yellow. Pistils: Pistil number: One. Pistil length: About 2 to 3 mm. Stigma shape: Slightly dome-like. Stigma color: Yellow. Ovary: Five-locular, green.

*Seed.*—Length, about 1 to 1.5 mm; diameter, about 0.2 mm.

Disease resistance: Plants of the new Leptospermum have exhibited good resistance to root pathogens common to Leptospermum.

Winter hardiness: Typical of the species.

It is claimed:

1. A new and distinct cultivar of Leptospermum plant named 'BY11', as illustrated and described.

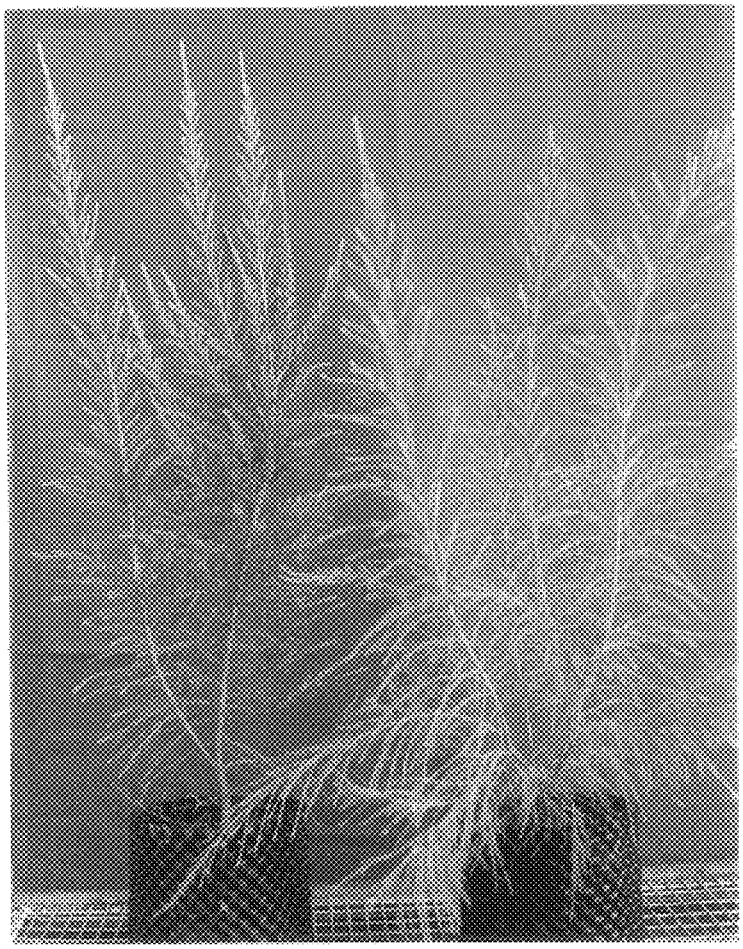
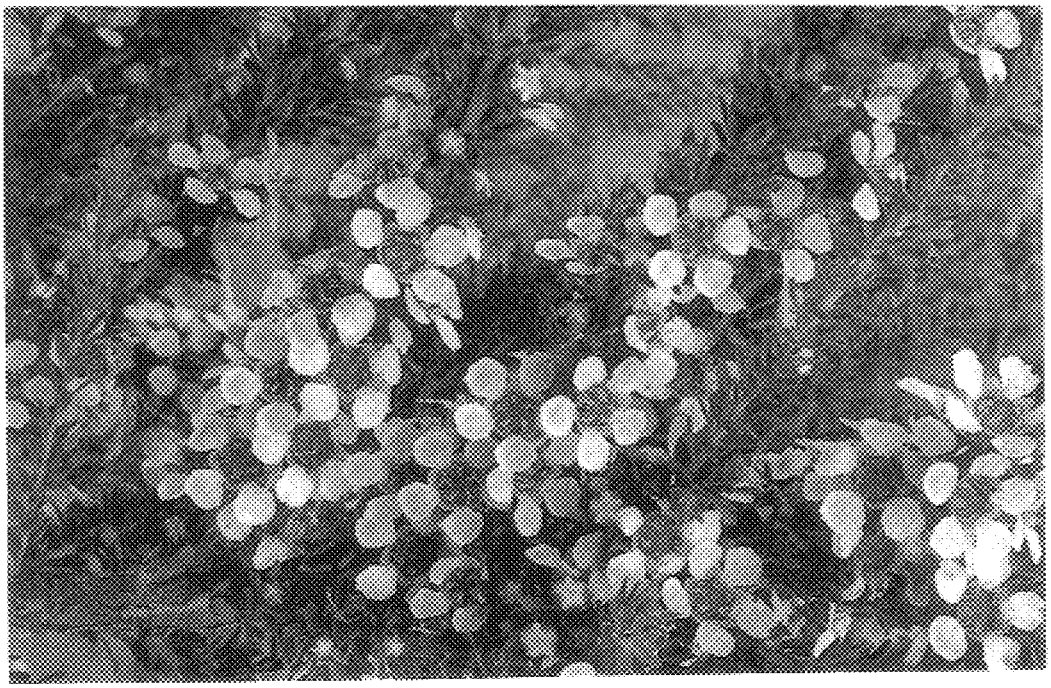

* * * * *